United States Patent [19]

Porcello

[11] Patent Number: 6,015,530
[45] Date of Patent: Jan. 18, 2000

[54] GENERAL APPLICABLE TOPICAL GERMICIDE

[76] Inventor: Joseph A. Porcello, 2600 S. Ocean Blvd., A-3, Boca Raton, Fla. 33432

[21] Appl. No.: 09/001,128

[22] Filed: Dec. 30, 1997

Related U.S. Application Data

[63] Continuation-in-part of application No. 08/593,615, Jan. 30, 1996.

[51] Int. Cl.⁷ .................................................. A01N 59/12
[52] U.S. Cl. ............................................. 422/37; 424/667
[58] Field of Search ................... 422/1, 28, 37; 424/667

[56] References Cited

U.S. PATENT DOCUMENTS

| | | | |
|---|---|---|---|
| 1,596,651 | 8/1926 | Bryant | 424/667 |
| 1,676,554 | 7/1928 | Hoopman | 424/667 |
| 1,767,667 | 6/1930 | Gray | 424/667 X |
| 1,800,502 | 4/1931 | Brown | 424/667 |
| 1,896,171 | 2/1933 | Harry | 424/667 |
| 3,301,752 | 1/1967 | Bubash | 424/667 |
| 4,006,218 | 2/1977 | Sipos | 424/54 |
| 4,081,396 | 3/1978 | Batterton | 424/670 X |
| 4,207,310 | 6/1980 | Langford | 424/670 |
| 4,290,846 | 9/1981 | Muntwyler | 162/161 |
| 4,321,257 | 3/1982 | Sipos | 424/667 X |
| 4,444,756 | 4/1984 | Schüssler et al. | 424/667 X |
| 4,766,113 | 8/1988 | West et al. | 514/187 |
| 4,903,583 | 2/1990 | Frazier | 422/306 X |
| 5,017,617 | 5/1991 | Kihara et al. | 514/635 |
| 5,154,920 | 10/1992 | Flesher et al. | 514/643 |
| 5,256,701 | 10/1993 | Tamura et al. | 424/667 X |
| 5,379,806 | 1/1995 | Matthews et al. | 138/149 |

OTHER PUBLICATIONS

Seymour S. Block, ed., *Disinfection, Sterilization, and Preservation*, 2 ed., 1977, at pp. 196–212, Lea & Febiger, Philadelphia, PA.

Ernest C. McCulloch, *Disinfection and Sterilization*, 1945, at pp. 345–346, Lea & Febiger, Philadelphia, PA.

*Primary Examiner*—Elizabeth McKane
*Attorney, Agent, or Firm*—Ted W. Whitlock

[57] ABSTRACT

A composition and method for disinfecting inanimate and dermal or mucous membrane skin surfaces includes phenol, iodine solution, and glycerin. In a most preferred embodiment, the solution includes, by volume, between about ½ and about 1 volume units phenol, between about ½ and about 2 volume units of iodine solution, between about 2 and about 8 volume units of glycerin. A suitable diluent such as water or glycerin can also be used. The iodine solution is preferably a tincture of iodine solution having, by volume, between about 2% and 10% iodine in ethyl alcohol, and about 5% potassium iodide.

20 Claims, No Drawings

GENERAL APPLICABLE TOPICAL GERMICIDE

CROSS-REFERENCE TO RELATED APPLICATION

This is a continuation-in-part of co-pending U.S. patent application, Ser. No. 08/593,615, filed Jan. 30, 1996.

FIELD OF THE INVENTION

This invention relates generally to a germicidal disinfectant, and more particularly to a general topical germicide or disinfectant for dermal surfaces or inanimate surfaces such as air ducts.

BACKGROUND OF THE INVENTION

The presence of microbes such as bacteria are an ever-present problem for humans. Microbes are the cause of a variety of ailments, including but not limited to: acne or other skin blemishes (e.g., pimples; canker sores; fever blisters; herpes (genital and non-genital); other sexually transmitted diseases (STDS); intertrigo, thrush, and gingivitis or other oral infections).

It has long been recognized that harmful microbes can be transmitted from a person carrying or infected with the organism to other persons through a variety of vectors, including air conditioning systems, direct contact with a non-disinfected site, or the like.

It has also been recognized that disinfecting formulations or compositions which are selective for particular microbes, e.g., standard antibiotics, can result in resistance by those microbes to the disinfecting composition. Accordingly, in areas where infection is rampant, and disinfection or treatments using antibiotics is extensive, e.g., in a hospital or other health care facility, resistant microbes can be more likely to be present and often are more pathogenic. This phenomenon is known as "nosocomial infection."

A recent report in the *Boston Globe* indicated that as many as 10% of the estimated 2 million infections that patients pick up in hospitals each year are due to *Pseudomonas aerugiosa*, a common bacteria that forced Children's Hospital in Boston, Massachusetts to close its neonatal ICU in August of 1997. The bacteria killed four newborns in a matter of weeks despite all control efforts. *The Palm Beach Post*, Sep. 16, 1997, p. 7A.

The rapid spread of bacteria and other microbes causing ill health among patients in hospitals will likely continue unless an effective germicide, also known as a "biocide", can be used to address the problem. The term "germicide" denotes a chemical agent that possesses antiseptic, disinfectant, or preservative activities. Germicides can have advantages over antibiotics which, typically, are far more specific in action and thus are more readily overcome by mutation. *ASM News* (1997) 63(9):481.

Common biocidal compounds currently in use include chlorhexidine acetate, gluconate, ethylene oxide, and glutaraldehyde. However, these germicides, though generally effective, can have particular disadvantages, including toxicity to humans or corrosiveness to skin, making them unsafe to handle without protective clothing.

Resorting to the use of previously known germicides, which are safer to handle than currently used biocides, also presents a risk due to the disadvantage inherent in those germicides, e.g., their lower efficacy against certain pathogenic organisms or their undesirable side effects of being corrosive, stinging, or staining to the skin.

Lugol's solution has long been known as having germicidal activity. However, Lugol's solution is composed only of 5% iodine and 10% potassium iodide in an aqueous solution. Lugol's solution does not have any other germicidal ingredient, e.g., ethanol or phenol, to enhance its germicidal effect or attenuate the staining effect of the iodine.

Boulton's solution, also a long known germicidal agent, is composed of Lugol's solution in combination with phenol and glycerin. Boulton's solution contains no ethanol, thus also missing an important ingredient which can enhance the germicidal activity and attenuate the corrosive nature of the phenol present in Boulton's solution. In addition, the preparation of the Boulton's solution requires a heating step. This heating of the mixture necessarily drives off a certain amount of the iodine and phenol, and further affects the iodine compound of the mixture as evidenced by the change in color (clearing) of the solution after heating.

It is therefore desirable to provide a novel formulation and method for controlling the spread of such microbes more efficaciously without causing harm or pain to either the person receiving treatment or handling the germicide.

SUMMARY OF THE INVENTION

It is an object of the invention to provide a composition and method for disinfecting dermal surfaces, particularly through topical applications, which is highly effective against pathogenic microorganisms yet safe to handle.

It is another object of the invention to provide a method for disinfecting inanimate surfaces such as metal, glass, ceramic and plastic, and particularly the interior surfaces of air ducts.

These and other objects are accomplished by a composition and method in which a disinfecting composition comprising phenol, tincture of iodine, and glycerin is provided. The mixture of these compounds can be used in varying concentrations or dilutions (syncrasies) and is typically diluted with potable water. The composition can be topically applied to dermal or mucosal surfaces. The composition will efficaciously disinfect the surfaces to control a number of microbe-associated problems.

The composition in a more concentrated syncrasy is also useful to disinfect the air ducts of heating, ventilation, and air conditioning (HVAC) systems. The solution can be misted by apparatus known in the art and caused to flow into the ducts, where it is carried by the flowing air through the ducts and deposited on interior duct surfaces. The composition can also be used to disinfect other inanimate objects such as laboratory instruments and instruments found in barber shops and beauty salons.

Phenol, iodine, and alcohol are known to have germicidal properties. Surprisingly, however, this particular combination and syncrasy of ingredients results in a composition which avoids certain of the disadvantages of those components if used alone or in other combinations different from the subject composition. For example, the corrosive nature of phenol, the irritative, blistering, and staining properties of iodine, and the stinging effect of ethyl alcohol are all attenuated or absent in this formulation of the subject invention. The germicidal activity of phenol, iodine, or alcohol, is not reduced. Moreover, the subject composition is biodegradable and non-carcinogenic.

The composition can be applied to the skin by a variety of methods, including applying directly as a solution, as a swab, by spray application, or through the incorporation of other compounds as carriers for an ointment. It is also possible to add additional ingredients. The composition has particular utility for disinfecting dermal or mucosal membrane surfaces. For example, the subject composition can be used to control acne or pimples, canker sores, fever blisters, or herpes. The composition can be utilized in many suitable concentrations, and in many possible syncrasies of the chemicals.

DETAILED DESCRIPTION OF THE PREFERRED EMBODIMENT

According to the invention, a method for disinfecting a dermal or mucosal surface, includes the steps of applying to the surface a disinfecting composition, which includes in a particular ratio of phenol, iodine, and glycerin. The composition is applied to the surface by suitable methods, including brush application, aerosol, ointments or liquid pump.

In a preferred embodiment, a standard mixture is prepared which includes glycerin, phenol and tincture of iodine. The standard mixture comprises between approximately ½–1 volume unit of phenol (USP), between approximately ½–2 volume units of 7% tincture of iodine solution (USP), and between approximately 2–8 volume units of glycerin (USP). Most preferably, the standard mixture comprises about 4 units of glycerin (USP). A currently preferred standard formula is as follows:

| | |
|---|---|
| glycerin (USP) | 4 volume units |
| 7% tincture of iodine (USP) | 1 volume unit |
| phenol (USP) | 1 volume unit |

The standard mixture can be diluted up to about thirty times with suitable diluents such as water or additional glycerin, as well as mixtures of such diluents, based upon bactericidal demand. The final composition, if used for dermal applications, preferably is undiluted and comprises 16–17% by volume of phenol, 16–17% by volume of tincture of iodine, and about 66–67% by volume of glycerin. One suitable composition that is useful for disinfecting inanimate surfaces is:

| | |
|---|---|
| phenol (USP) | 1 oz. = 16.665% |
| 7% tincture of iodine (USP) | 1 oz. = 16.665% |
| glycerin (USP) | 4 oz. = 66.670% |

The concentration can be increased if a high bacteria count is present.

The iodine solution can be formulated as a tincture of iodine solution comprising, by volume, between about 2% and 10% iodine, about 5% potassium iodide (for stabilization), and the remainder ethyl alcohol. In a most preferred embodiment, the iodine solution is about 7% tincture of iodine (USP).

Compositions according to the invention can be applied to a surface by any suitable method. The application to air ducts can be made by any suitable means, as by a brush or roller, but is preferably atomized and propelled onto the surface by a pump or other suitable mode of force.

The invention also has utility for disinfecting dermal surfaces. The above-described composition, with the addition of 10 oz. of water, can be applied to such skin surfaces to control microbe related problems such as pimples, canker sores, fever sores, herpes (genital and otherwise), and for local lavage of genitals after sexual intercourse to prevent sexual associated infections, for control and treatment of anal and perineal area infections, for control of local itchiness and pruritus, for control and treatment of intertrigo, for control and treatment of thrush, for control and treatment of gingivitis, and for pain abatement and control of infection associated with infected teeth. The composition of the subject invention can be swabbed in the nares to control sinus infection or to desensitize the nasal lining to allergenic pollens; can be used to treat or control infection of the vaginal canal using a tampon saturated with a solution of the subject composition; and can be used to treat infections in the mouth by applying the subject composition to the buccal cavity.

In the application to dermal surfaces, the application can be made directly as an ointment, or by other suitable application methods known in the art. For example, the composition can be provided as a saturant in a disposable wipe, as an ointment, or other suitable application. The invention can be used in different concentrations, and in all possible syncrasies.

The composition of the subject invention can provide a plurality of advantages. For example, the combination of ingredients comprising the subject composition attenuates the corrosive action of phenol; the blistering, irritative and staining action of iodine; and the stinging action of the ethanol used in the tincture of iodine solution. Thus, the composition provides an effective germicide which is not corrosive, blistering, irritative, staining, or stinging to the handler or the patient on which the composition is applied. Further, because the composition utilizes components which are ubiquitous in the natural environment and known to be non-carcinogenic, the composition can be used without fear of causing cancer in the patient or in health workers that may apply the solution to the patient. The volatility of the composition provides a disinfectant which evaporates from the surface and leaves no residue.

The germicidal activity of the subject composition is retained and has been shown to be an effective bacteriocidal mixture against nosocomial bacteria, e.g., *Pseudomonas aeruginosa* and *Staphylococcus aureus*.

In order to assay the effectiveness of the subject composition, various dilution levels were tested against different microbial targets. A use dilution assay was carried out utilizing a direct plating technique with direct contact of stainless steel penicillin caps onto the plate. The control disinfectant is 100% and 90% phenol. This assay was adopted in order to assay effectiveness against different organisms which were cultured under various media conditions. All assays were performed in quadruplicate and average values of the Zone of Inhibition determined.

The assay was carried out with modifications based on the Official Methods of Analysis of the Association of Official Analytical Chemists (AOAC), Fourteenth Edition, 1984; Use Dilution Method, Final Action, Chapter 4, pp. 67–68. Working solutions of the concentrated products were made at levels specified, a 1:1 dilution level indicating a concentrated solution with no dilution. The stainless steel discs were immersed in the disinfectant and placed onto inoculated solid media appropriate to each organism examined. The Zone of Inhibition was measured as the diameter of the effective area of anti-bacterial activity. The product dilutions were made using laboratory de-ionized, purified water (USP Type 1 Water). The subject composition was assayed against the following microbiological Organisms:

| Organism | ATCC Accession No. |
|---|---|
| *Escherichia coli* | 8739 |
| *Pseudomonas aeruginosa* | 9027 |
| *Staphylococcus aureus* | 6538 |
| *Neisseria gonorrhoeae* | 9826 |
| *Haemophilus influenza* | 35056 |
| *Klebsiella pneumoniae* | 8047 |
| *Streptococcus pneumoniae* | 12213 |
| *Salmonella typhi* | 6539 |

The test organisms were cultured and passed at least five times prior to testing. Initial dilutions of all cultures were made from a 24 hour inoculum. Tests were performed in duplicate and repeated to insure measurement precision. The results of these tests showed the subject composition to have bacteriocidal activity comparable to phenol. The details of the studies and results are provided in the Examples section hereinbelow.

The following examples illustrate procedures for practicing the invention. These examples should not be construed as limiting. All percentages are by weight and all solvent mixture proportions are by volume unless otherwise noted.

EXAMPLE 1

Use Dilution Assay for Diluted Composition

The assay was carried out to confirm Phenol Coefficient Results and to determine maximum dilutions effective for practical disinfection with modifications based on the Official Methods of Analysis of the Association of Official Analytical Chemists (AOAC), Fourteenth Edition, 1984; Use Dilution Method, Final Action, Chapter 4, pp. 67–68. Working solutions of the concentrated products were made at levels specified, a 1:1 dilution level indicating a concentrated solution with no dilution. The stainless steel discs were immersed in the disinfectant and placed onto inoculated solid media appropriate to each organism examined. The Zone of Inhibition was measured as the diameter of the effective area of anti-bacterial activity. The product dilutions were made using laboratory de-ionized, purified water (USP Type I Water). Activity of the subject composition was assayed against the following organisms:

| Organism | ATCC Accession No. |
|---|---|
| *Escherichia coli* | 8739 |
| *Pseudomonas aeruginosa* | 9027 |
| *Staphylococcus aureus* | 6538 |
| *Neisseria gonorrhoeae* | 9826 |
| *Haemophilus influenza* | 35056 |
| *Klebsiella pneumoniae* | 8047 |
| *Streptococcus pneumoniae* | 12213 |
| *Salmonella typhi* | 6539 |

The test organisms were cultured and passed at least five times prior to testing. Initial dilutions of all cultures were made from a 24 hour inoculum. Tests were performed in duplicate and repeated to insure measurement precision.

Test Composition (Product 1 15): 1 part phenol, 1 part 7% tincture of iodine, 4 parts glycerin, and 10 parts water at serial dilutions of (1:1), (1:148), (1:1000).

| Concentration | Target Organism | Zone of Inhibition (mm) | Ratio to Phenol (90%) |
|---|---|---|---|
| 1:1 | *Staphylococcus aureus* | 15 mm | 0.7500 |
| 1:1 | *Strep. pneumonia* | 22 mm | 0.5116 |
| 1:1 | *E. coli* | 14 mm | 0.6087 |
| 1:1 | *H. influenza* | 21 mm | 0.5385 |
| 1:1 | *Klebsialla pneumonia* | 17 mm | 0.4722 |
| 1:1 | *Neisseria gonorrhae* | 36 mm | 0.7826 |
| 1:1 | *Pseudomonas aeruginosa* | 14 mm | 0.7777 |
| 1:1 | *Salmonella typhimurium* | 16 mm | 0.5161 |
| 1:100 | *Strep. pneumonia* | 12 mm | |
| 1:100 | *H. influenza* | no inhibition | |
| 1:100 | *Klebsialla pneumonia* | 17 mm | |
| 1:100 | *Neisseria gonorrhae* | 12 mm | |
| 1:100 | *Salmonella typhimurium* | no inhibition | |
| 1:148 | *Staphylococcus aureus* | no inhibition | |
| 1:148 | *E. coli* | no inhibition | |
| 1:148 | *Pseudomonas aeruginosa* | no inhibition | |
| 1:1000 | *Staphylococcus aureus* | no inhibition | |
| 1:1000 | *E. coli* | no inhibition | |
| 1:1000 | *Pseudomonas aeruginosa* | no inhibition | |

The results indicated that the composition exhibited significant anti-bacterial activity against the organisms tested. The Disinfectants examined showed a Ratio of Inhibition to Phenol (90%) consistent to the concentration gradient of the disinfectants analyzed.

EXAMPLE 2

Use Dilution Assay for Undiluted Composition

The assay was carried out under conditions as stated in Example 1, above, but without serial dilutions of 1:148 or 1:1000.

Test Composition (Product 114): 1 part phenol, 1 part 7% tincture of iodine, and 4 parts glycerin.

| Concentration | Target Organism | Zone of Inhibition (mm) | Ratio to Phenol (90%) |
|---|---|---|---|
| 1:1 | *Staphylococcus aureus* | 18 mm | |
| 1:1 | *Strep. pneumonia* | 22 mm | |
| 1:1 | *E. coli* | 18 mm | |
| 1:1 | *H. influenza* | 21 mm | |
| 1:1 | *Klebsialla pneumonia* | 17 mm | |
| 1:1 | *Neisseria gonorrhae* | 36 mm | |
| 1:1 | *Pseudomonas aeruginosa* | 18 mm | |
| 1:1 | *Salmonella typhimurium* | 16 mm | |
| 1:1 | *Staphylococcus aureus* | 18 mm | 0.9000 |
| 1:1 | *Strep. pneumonia* | 22 mm | 0.5116 |
| 1:1 | *E. coli* | 18 mm | 0.7826 |
| 1:1 | *H. influenza* | 21 mm | 0.5385 |
| 1:1 | *Klebsialla pneumonia* | 17 mm | 0.4722 |
| 1:1 | *Neisseria gonorrhae* | 36 mm | 0.7826 |
| 1:1 | *Pseudomonas aeruginosa* | 18 mm | 1.0000 |
| 1:1 | *Salmonella typhimurium* | 16 mm | 0.5161 |

EXAMPLE 3

Use Dilution Assay for Concentrated Composition

The assay was carried out under conditions as stated in Example 1, above, but without serial dilutions.

Test Composition (Product 112): 1 part phenol, 1 part 7% tincture of iodine, and 2 parts glycerin.

| Concentration | Target Organism | Zone of Inhibition (mm) | Ratio to Phenol (90%) |
|---|---|---|---|
| 1:1 | Staphylococcus aureus | 20 mm | 1.0000 |
| 1:1 | Strep. pneumonia | 27 mm | 0.6279 |
| 1:1 | E. coli | 22 mm | 0.9565 |
| 1:1 | H. influenza | 29 mm | 0.7436 |
| 1:1 | Klebsialla pneumonia | 20 mm | 0.5555 |
| 1:1 | Neisseria gonorrhae | 37 mm | 0.8043 |
| 1:1 | Pseudomonas aeruginosa | 24 mm | 1.3333 |
| 1:1 | Salmonella typhimurium | 18 mm | 0.5806 |

The results indicated that the composition exhibited significant anti-bacterial activity against the organisms tested. The compositions examined showed a Ratio of Inhibition to Phenol (90%) consistent to the concentration gradient of the compositions analyzed.

This invention can take other specific forms without departing from the spirit or essential attributes thereof, and accordingly, reference should be had to the following claims, rather than the foregoing specification, as indicating the scope of the invention.

I claim:

1. A method for disinfecting a dermal or mucous membrane surface comprising the steps of providing a composition which is stingless, stainless, and non-irritative to skin or clothing, said composition consisting essentially of, by volume of the total composition; about one volume units phenol; about one volume units 7% tincture of iodine solution; and about four to about eight volume units glycerin; and applying to said surface an effective amount of said composition.

2. The method of claim 1, wherein said composition comprises about 4 volume units of glycerin.

3. The method of claim 1, wherein said composition further comprises a diluent.

4. The method of claim 3, wherein said diluent is selected from the group consisting of water and glycerin, and mixtures thereof.

5. The method of claim 4, wherein said diluent comprises between about 10 volume units and about 100 volume units.

6. The method of claim 1, wherein said iodine solution comprises between about 2 % and about 10 % iodine, about 5% potassium iodide, and the remainder ethyl alcohol.

7. The method of claim 1, wherein said iodine solution is about 7% tincture of iodine (USP) solution.

8. The method of claim 1, wherein said composition is applied to said dermal or mucous membrane surface to control microbe related problems selected from the group consisting of pimples, canker sores, fever sores, and herpes.

9. The method of claim 1, wherein said composition is applied to said dermal surface for local lavage of the genitals after sexual intercourse.

10. The method of claim 1, wherein said composition is applied to said dermal surface for the control and treatment of anal and perineal area infections.

11. The method of claim 1, wherein said composition is applied to said dermal surface to control local itching and pruritus.

12. The method of claim 1, wherein said composition is applied to said dermal surface for control and treatment of intertrigo.

13. The method of claim 1, wherein said composition is applied to said dermal gum surface for control and treatment of thrush.

14. The method of claim 1, wherein said composition is applied to said dermal gum surface for control and treatment of gingivitis.

15. The method of claim 1, wherein said composition is applied to said dermal gum surface for pain abatement and the control of infection associated with infected teeth.

16. The method of claim 1, wherein said composition is applied to the nares for sinus infection or allergy relief; to the vaginal canal to treat or control vaginal infection; and to the buccal cavity to treat oral infection.

17. A composition for disinfecting a dermal or mucous membrane surface, said composition consisting essentially of, by volume of the total composition: about one volume units phenol; about one volume units 7% tincture of iodine solution; and about four to about eight volume units glycerin; and wherein said composition is stingless, stainless, and non-irritative to skin or clothing.

18. The composition of claim 17, wherein said composition comprises about 4 volume units of glycerin.

19. The composition of claim 17, wherein said iodine solution is about 7% tincture of iodine.

20. The composition of claim 17, wherein said composition further comprises a diluent.

* * * * *